United States Patent
Konishi et al.

(10) Patent No.: US 6,495,730 B1
(45) Date of Patent: Dec. 17, 2002

(54) CATALYSTS FOR HYDROGENATION OF CARBOXYLIC ACID

(75) Inventors: Mitsuo Konishi, Okayama (JP); Eizaburou Ueno, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/088,212

(22) PCT Filed: Sep. 21, 2000

(86) PCT No.: PCT/JP00/06473
§ 371 (c)(1), (2), (4) Date: Mar. 15, 2002

(87) PCT Pub. No.: WO01/21306
PCT Pub. Date: Mar. 29, 2001

(30) Foreign Application Priority Data

Sep. 21, 1999 (JP) ............................................. 11-267268

(51) Int. Cl.$^7$ ............................................... C07C 31/13
(52) U.S. Cl. ........................ 568/831; 568/864; 568/885
(58) Field of Search ................................ 568/864, 885, 568/831

(56) References Cited

U.S. PATENT DOCUMENTS

| | | | |
|---|---|---|---|
| 4,359,404 A | * | 11/1982 | Grey |
| 5,149,680 A | * | 9/1992 | Kitson |
| 5,426,246 A | * | 6/1995 | Nagahara |
| 5,478,952 A | * | 12/1995 | Schwartz |
| 5,496,786 A | * | 3/1996 | Gubitosa |
| 5,969,194 A | * | 10/1999 | Hara |
| 6,008,384 A | | 12/1999 | Bochrath et al. |
| 6,018,048 A | * | 1/2000 | Morikawa |
| 6,294,703 B1 | * | 9/2001 | Hara |

FOREIGN PATENT DOCUMENTS

| | | |
|---|---|---|
| EP | 747321 | 12/1996 |
| JP | A-5-246915 | 9/1993 |
| JP | A-11-60523 | 3/1999 |
| JP | A-11-199530 | 7/1999 |
| WO | WO 88/07515 | 6/1988 |
| WO | WO 93/14866 | 8/1993 |
| WO | WO 96/27436 | 9/1996 |

* cited by examiner

Primary Examiner—Michael L. Shippen
(74) Attorney, Agent, or Firm—Birch, Stewart, Kolasch & Birch, LLP

(57) ABSTRACT

Disclosed is a catalyst for hydrogenating a carboxylic acid, comprising an activated carbon having carried thereon an active metal species comprising ruthenium and tin, wherein the activated carbon is produced by subjecting a carbonaceous material to activation treatment using zinc chloride, followed by calcination. Also disclosed is a catalyst for hydrogenating a carboxylic acid, comprising an activated carbon having carried thereon an active metal species comprising ruthenium and tin, wherein the activated carbon, prior to having carried thereon the active metal species, exhibits specific pore characteristics wherein, especially, the pore volume with respect to pores each having a radius of from 10 to 100 Å is from 0.5 to 2.0 cm$^3$/g. Further disclosed is a method for producing a primary alcohol, which comprises reacting at least one starting material selected from the group consisting of a carboxylic acid and a carboxylic anhydride with hydrogen gas in the presence of water and the above-mentioned catalyst to thereby effect a catalytic hydrogenation of the starting material.

18 Claims, No Drawings

CATALYSTS FOR HYDROGENATION OF CARBOXYLIC ACID

This application is the national phase under 35 U.S.C. § 371 of PCT International Application No. PCT/JP00/06473 which has an International filing date of Sep. 21, 2000, which designated the United States of America.

BACKGROUND OF THE INVENTION

1. Field of the Invention

The present invention relates to a catalyst for hydrogenating a carboxylic acid. More particularly, the present invention is concerned with a catalyst for hydrogenating a carboxylic acid, which comprises a specific activated carbon having carried thereon an active metal species comprising ruthenium and tin. By the use of the catalyst of the present invention, a primary alcohol can be efficiently produced directly from a carboxylic acid or carboxylic anhydride by hydrogenation thereof, not through esterification thereof. Further, the catalyst of the present invention can be applied to the hydrogenation of a wide variety of carboxylic acids. Therefore, the catalyst of the present invention is extremely advantageous from the commercial viewpoint. The present invention is also concerned with a method for producing a primary alcohol, which comprises reacting at least one starting material selected from the group consisting of a carboxylic acid and a carboxylic anhydride with hydrogen gas in the presence of water and the above-mentioned catalyst to thereby effect a catalytic hydrogenation of the starting material.

2. Prior Art

The term "alcohol" is a general term covering organic compounds having a hydroxyl group. An extremely large number of alcohols exist. Many of the alcohols are very important compounds which are widely used in various industrial fields. These many important alcohols are commercially produced in large amounts.

Examples of alcohols having one hydroxyl group (monohydric alcohols) include methanol, ethanol, n-propanol and the like. Many monohydric alcohols are frequently used as a raw material for chemical synthesis or as a solvent. Examples of alcohols having two hydroxyl groups (dihydric alcohols or diols) include ethylene glycol, propylene glycol, 1,4-butanediol and the like. Many dihydric alcohols are useful as a raw material for producing a polyester, a polyurethane and the like.

A large number of methods for producing alcohols are conventionally known. Commercial production of primary alcohols (alcohols having a hydroxymethyl group ($—CH_2OH$)) is performed mainly by any of the following two methods: a method in which an olefin is subjected to a hydration reaction and a method in which a carboxylic ester is subjected to a hydrogenation reaction in the presence of a copper-containing catalyst under high temperature and high pressure conditions.

Of these two methods, the method in which an olefin is subjected to a hydration reaction is mainly used for producing ethanol. However, this method cannot be used for producing an alcohol having 3 or more carbon atoms, such as n-propanol, n-butanol or 1,4-butanediol. Therefore, these alcohols must be produced by the method in which a carboxylic ester (hereinafter, simply referred to as an "ester") is subjected to a hydrogenation reaction. Hereinbelow, an explanation is made with respect to the production of a primary alcohol by this method involving hydrogenation of an ester, wherein, in the explanation, production of 1,4-butanediol is taken as an example.

At present, 1,4-butanediol is produced from n-butane. Although it is not impossible to produce 1,4-butanediol by introducing two hydroxyl groups into n-butane by a one-step reaction, such a reaction is extremely disadvantageous from an economical viewpoint. Therefore, it is virtually impossible to produce 1,4-butanediol on a commercial scale by the above-mentioned one-step reaction. For this reason, at present, 1,4-butanediol is produced from n-butane by a method comprising:

subjecting n-butane to air oxidation to produce succinic acid, maleic acid, succinic anhydride or maleic anhydride, especially maleic acid or maleic anhydride; and producing 1,4-butanediol from the thus produced acid or acid anhydride.

In general, a carboxylic acid can be easily converted to a primary alcohol by a reduction reaction. In a reduction reaction, generally, an appropriate reducing agent is used. However, usually, a reduction reaction of a carboxylic acid requires the use of a strong reducing agent having extremely high reactivity, such as lithium aluminum hydride. Special care must be taken in the handling and storage of such a strong reducing agent. Therefore, such a strong reducing agent is not suitable for use in the commercial scale production of a primary alcohol.

On the other hand, the so-called hydrogenation reaction, i.e., a reduction reaction performed using hydrogen gas (as a reducing agent) and an appropriate catalyst, is suitable for being practiced on a commercial scale. However, usually, the hydrogenation reaction cannot be applied to the reduction of a carboxylic acid. This is because the conventional catalyst used for hydrogenation is soluble in a carboxylic acid, so that the catalyst activity of the catalyst cannot be maintained in the presence of a carboxylic acid.

Therefore, at present, the production of 1,4-butanediol is performed by a method in which maleic acid or maleic anhydride (obtained by air oxidation of n-butane) is esterified with an appropriate alcohol, and the resultant ester is subjected to a hydrogenation reaction in the presence of a copper-containing catalyst under high temperature and high pressure conditions, to thereby convert the ester to 1,4-butanediol.

The method for producing an alcohol by the hydrogenation of an ester in the presence of a copper-containing catalyst under high temperature and high pressure conditions is described in, for example, Japanese Patent Application prior-to-examination Publication (Kohyo) No. 2000-510837 (corresponding to U.S. Pat. No. 6,100,410), Japanese Patent Application prior-to-examination Pubication (Kohyo) No. 2000-510475 (corresponding to U.S. Pat. No. 6,077,964), Japanese Patent Application prior-to-examination Pubication (Kohyo) No. 2000-506134 (corresponding to U.S. Pat. No. 5,981,769), Unexamined Japanese Patent Application Laid-Open Specification No. 7-196558 (corresponding to U.S. Pat. No. 5,414,159) and U.S. Pat. No. 5,334,779.

However, in this method, three steps (i.e., production of a carboxylic acid, esterification of the produced carboxylic acid, and hydrogenation of the produced ester) are required, so that the process for producing a primary alcohol inevitably becomes complicated. The complicated process poses a problem in that the process needs a number of pieces of equipment, such as the equipment for the esterification of the carboxylic acid and the equipment for separating, recovering and recycling the alcohol which is used in the esterification of the carboxylic acid and by-produced in the hydrogenation of the ester.

Because of this problem, it is apparent that the production of a primary alcohol by the hydrogenation of an ester is disadvantageous from the viewpoint of the production cost and the like. Therefore, various studies have been made with respect to the method for shortening the process for producing a primary alcohol.

As an example of such a method, there can be mentioned a method in which a carboxylic acid (but not an ester thereof) is directly subjected to hydrogenation using a catalyst which can maintain its catalyst activity even in the presence of an acid, to thereby obtain a primary alcohol.

In this method, a primary alcohol can be obtained by a two-step reaction, i.e., a process comprising the production of a carboxylic acid and the hydrogenation of the produced carboxylic acid. In this method, esterification of a carboxylic acid (wherein the esterification is required in the conventional process) is not required, so that equipment for this esterification is not required. Further, since this method does not involve esterification, this method is free from the problem that an alcohol (used in the esterification) is by-produced in the hydrogenation, and therefore this method does not need equipment for recovering and recycling the by-produced alcohol. As a result, the process for producing a primary alcohol can be shortened, and the equipment required for practicing the process can be considerably simplified.

For the above-mentioned reason, there is a demand for a catalyst which can be used for the direct hydrogenation of a carboxylic acid (but not via esterification thereof) and which exhibits high activity and can be used for the hydrogenation of various carboxylic acids and can maintain its activity even in the presence of an acid. Further, there is also a demand for a method for efficiently producing a primary alcohol by subjecting a carboxylic acid to hydrogenation in the presence of the above-mentioned catalyst.

A number of proposals have been made with respect to catalysts for use in the hydrogenation of a carboxylic acid to produce a primary alcohol and with respect to methods for producing a primary alcohol using such catalysts. Some of these proposals are concerned with methods for producing 1,4-butanediol by the direct hydrogenation of succinic acid or maleic acid. In these methods, usually, the hydrogenation is performed in the presence of water. Only the catalyst systems used in these methods are enumerated below.

A catalyst comprising a ruthenium-iron oxide (U.S. Pat. No. 4,827,001);

A catalyst comprising a porous carbon having carried thereon ruthenium-tin, wherein the BET specific surface area (as determined by the application of the Brunauer-Emmett-Teller adsorption isotherm) of the porous carbon is 2000 $m^2/g$ or more (Unexamined Japanese Patent Application Laid-Open Specification No. 5-246915);

A catalyst comprising silica having carried thereon ruthenium and tin, wherein the silica has been modified with titanium and/or alumina (Unexamined Japanese Patent Application Laid-Open Specification No. 6-116182);

A catalyst comprising a carrier having carried thereon ruthenium, tin and a compound selected from the group consisting of an alkali metal compound and an alkaline earth metal compound (Unexamined Japanese Patent Application Laid-Open Specification No. 6-239778);

A catalyst comprising a carrier having carried thereon tin and at least one metal selected from the group consisting of ruthenium, platinum and rhodium (Unexamined Japanese Patent Application Laid-Open Specification No. 7-165644);

A catalyst comprising a carrier having carried thereon ruthenium and tin (Unexamined Japanese Patent Application Laid-Open Specification No. 9-12492) (In the method using this catalyst, the hydrogenation is performed while feeding an excess amount of hydrogen gas into the reaction system and withdrawing, from the reaction system, the unreacted hydrogen gas entraining the hydrogenation product.);

A catalyst comprising a carrier having carried thereon ruthenium-tin-platinum (Unexamined Japanese Patent Application Laid-Open Specification No. 9-59190);

A catalyst comprising an activated carbon having carried thereon ruthenium-tin-platinum, wherein the catalyst is prepared by a method comprising impregnating an activated carbon with a solution of a carbonyl compound having 5 or less carbon atoms and metal components to be carried on the activated carbon (Unexamined Japanese Patent Application Laid-Open Specification No. 10-15388); and A catalyst comprising an activated carbon having carried thereon ruthenium-tin-platinum, wherein the activated carbon, prior to having carried thereon the metals, has been contacted with nitric acid (Unexamined Japanese Patent Application Laid-Open Specification No. 10-71332).

However, in any of the methods using the above-enumerated catalysts, considerable amounts of tetrahydrofuran and γ-butyrolactone are by-produced, so that the selectivity for and yield of desired 1,4-butanediol are not satisfactory.

Unexamined Japanese Patent Application Laid-Open Specification No. 7-82190 proposes a method for producing a primary alcohol, in which a carboxylic acid is subjected to hydrogenation in a tertiary alcohol as a solvent in the presence of a catalyst comprising a palladium compound and a rhenium compound. However, in this method, the reaction rate is not satisfactory.

It is conventionally known that, with respect to a catalyst comprising a carrier having carried thereon a catalyst component, the activity of the catalyst can be greatly altered by changing the properties of the carrier (for example, the pore distribution, the specific surface area, and the type of the pretreatment performed before the carrier has carried thereon the catalyst component). Therefore, with respect also to the properties of the catalyst for use in the hydrogenation of a carboxylic acid to produce a primary alcohol, various studies have been made for improving the yield of the primary alcohol, wherein the studies are focused on, for example, the specific surface area of the carrier (especially an activated carbon) and the method for the pretreatment of the carrier.

It is known that these conventional catalysts are useful in the hydrogenation of a limited type of carboxylic acid. However, there has been no knowledge as to whether or not these catalysts are also useful in the hydrogenation of a carboxylic acid other than the limited type of carboxylic acid.

For example, U.S. Pat. No. 5,698,749 states that, when maleic acid is subjected to hydrogenation using a catalyst comprising an activated carbon having carried thereon palladium-silver-rhenium, wherein the activated carbon, prior to having carried thereon the metals, has been subjected to nitric acid oxidation treatment, 1,4-butanediol can be obtained in a relatively high yield. However, this patent document does not describe at all the results of a reaction wherein, in the presence of this catalyst, a carboxylic acid other than maleic acid, such as glutaric acid or adipic acid, is subjected to hydrogenation.

Unexamined Japanese Patent Application Laid-Open Specification No. 11-60523 (corresponding to U.S. Pat. No.

5,969,194) states that, when adipic acid is subjected to hydrogenation using a catalyst comprising an activated carbon having carried thereon ruthenium-tin-platinum, wherein the activated carbon, prior to having carried thereon the metals, has been subjected to acid treatment, 1,6-hexanediol can be obtained from adipic acid in a high yield. However, the catalyst used in this patent document (i.e., a catalyst comprising an activated carbon having carried thereon ruthenium-tin-platinum) is substantially the same as that used in the above-mentioned Unexamined Japanese Patent Application Laid-Open Specification No. 10-71332. Therefore, in the case of the use of this catalyst, it is difficult to produce 1,4-butanediol from succinic acid or maleic acid with a high selectivity and in a high yield.

As apparent from the above, no catalyst has conventionally been known for use in the direct hydrogenation of a carboxylic acid (but not via esterification thereof) to produce a primary alcohol, wherein the catalyst can be applied to the hydrogenation of a wide variety of carboxylic acids; and no method has conventionally been known for producing a primary alcohol from a carboxylic acid by hydrogenation using such an excellent catalyst.

SUMMARY OF THE INVENTION

In this situation, the present inventors have made extensive and intensive studies with a view toward developing a catalyst for use in the direct hydrogenation of a carboxylic acid (but not via esterification thereof), wherein the catalyst exhibits high activity and can be applied to the hydrogenation of a wide variety of carboxylic acids and can maintain its activity even in the presence of an acid, and with a view toward developing a method for efficiently producing a primary alcohol by subjecting a carboxylic acid to hydrogenation in the presence of such an excellent catalyst. As a result, it has unexpectedly been found that a catalyst comprising a specific activated carbon having carried thereon an active metal species comprising ruthenium and tin exhibits a catalyst activity for effecting the direct hydrogenation of a carboxylic acid to produce a primary alcohol, and that this catalyst activity can be maintained even in the presence of an acid.

Further, it has also unexpectedly been found that the above-mentioned catalyst can be applied to the hydrogenation of a wide variety of carboxylic acids, especially dicarboxylic acids, such as succinic acid, glutaric acid and adipic acid, and that, by the hydrogenation, the desired primary alcohol can be obtained in high yield.

The present invention has been completed, based on these novel findings.

Accordingly, it is a primary object of the present invention to provide a catalyst for use in the direct hydrogenation of a carboxylic acid (but not via esterification thereof), wherein the catalyst exhibits high activity and can be applied to the hydrogenation of a wide variety of carboxylic acids and can maintain its activity even in the presence of an acid.

Another object of the present invention is to provide a method for efficiently producing a primary alcohol by subjecting a carboxylic acid to hydrogenation using the above-mentioned catalyst.

The foregoing and other objects, features and advantages of the present invention will be apparent to those skilled in the art from the following detailed description and the appended claims.

DETAILED DESCRIPTION OF THE INVENTION

In one aspect of the present invention, there is provided a catalyst for hydrogenating a carboxylic acid, comprising an activated carbon having carried thereon an active metal species comprising ruthenium and tin, wherein the activated carbon is produced by subjecting a carbonaceous material to activation treatment using zinc chloride, followed by calcination.

In another aspect of the present invention, there is provided a catalyst for hydrogenating a carboxylic acid, comprising an activated carbon having carried thereon an active metal species comprising ruthenium and tin, wherein the activated carbon, prior to having carried thereon the active metal species, exhibits the following properties (a) to (d):

(a) the total pore volume is from 1.2 to 3.0 cm$^3$/g;

(b) the pore volume with respect to pores each having a radius of less than 10 Å is from 0.03 to 0.8 cm$^3$/g;

(c) the pore volume with respect to pores each having a radius of from 10 to 100 Å is from 0.5 to 2.0 cm$^3$/g; and (d) the specific surface area is from 800 to less than 2000 m$^2$/g.

For easy understanding of the present invention, the essential features and various preferred embodiments of the present invention are enumerated below.

1. A catalyst for hydrogenating a carboxylic acid, comprising an activated carbon having carried thereon an active metal species comprising ruthenium and tin, wherein the activated carbon is produced by subjecting a carbonaceous material to activation treatment using zinc chloride, followed by calcination.

2. The catalyst according to item 1 above, wherein the active metal species further comprises at least one metal selected from the group consisting of rhenium, molybdenum, platinum, palladium, silver and nickel.

3. A catalyst for hydrogenating a carboxylic acid, comprising an activated carbon having carried thereon an active metal species comprising ruthenium and tin, wherein the activated carbon, prior to having carried thereon the active metal species, exhibits the following properties (a) to (d):

(a) the total pore volume is from 1.2 to 3.0 cm$^3$/g;

(b) the pore volume with respect to pores each having a radius of less than 10 Å is from 0.03 to 0.8 cm$^3$/g;

(c) the pore volume with respect to pores each having a radius of from 10 to 100 Å is from 0.5 to 2.0 cm$^3$/g; and (d) the specific surface area is from 800 to less than 2000 m$^2$/g.

4. The catalyst according to item 3 above, wherein the active metal species further comprises at least one metal selected from the group consisting of rhenium, molybdenum, platinum, palladium, silver and nickel.

5. A method for producing a primary alcohol, which comprises reacting at least one starting material selected from the group consisting of a carboxylic acid and a carboxylic anhydride with hydrogen gas in the presence of water and a catalyst to thereby effect a catalytic hydrogenation of the starting material, the catalyst comprising an activated carbon having carried thereon an active metal species comprising ruthenium and tin, wherein the activated carbon is produced by subjecting a carbonaceous material to activation treatment using zinc chloride, followed by calcination.

6. The method according to item 5 above, wherein the active metal species further comprises at least one metal selected from the group consisting of rhenium, molybdenum, platinum, palladium, silver and nickel.

7. The method according to item 5 or 6 above, wherein the starting material is at least one compound selected from the group consisting of a dicarboxylic acid represented by the following formula (1):

$$HOOC-R^1-COOH \tag{1}$$

wherein $R^1$ is a $C_2$–$C_{20}$ divalent hydrocarbon group, and a cyclic carboxylic anhydride represented by the following formula (2):

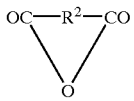
(2)

wherein $R^2$ is a $C_2$–$C_{20}$ divalent hydrocarbon group.

8. The method according to any one of items 5 to 7 above, wherein the starting material is at least one compound selected from the group consisting of succinic acid, glutaric acid, adipic acid, cyclohexane dicarboxylic acid, maleic acid, fumaric acid, terephthalic acid, succinic anhydride and maleic anhydride.

9. The method according to any one of items 5 to 8 above, wherein the starting material is a dicarboxylic acid mixture comprising succinic acid, glutaric acid and adipic acid.

10. The method according to item 9 above, wherein the dicarboxylic acid mixture is derived from a reaction mixture obtained by subjecting at least one compound selected from the group consisting of cyclohexanone and cyclohexanol to oxidation reaction.

11. The method according to any one of items 5 to 10 above, wherein the catalytic hydrogenation is conducted under conditions wherein the temperature is from 100 to 300° C. and the hydrogen pressure is from 1 to 25 MPa.

12. A method for producing a primary alcohol, which comprises reacting at least one starting material selected from the group consisting of a carboxylic acid and a carboxylic anhydride with hydrogen gas in the presence of water and a catalyst to thereby effect a catalytic hydrogenation of the starting material, the catalyst comprising an activated carbon having carried thereon an active metal species comprising ruthenium and tin, wherein the activated carbon, prior to having carried thereon the active metal species, exhibits the following properties (a) to (d):

(a) the total pore volume is from 1.2 to 3.0 cm³/g;
(b) the pore volume with respect to pores each having a radius of less than 10 Å is from 0.03 to 0.8 cm³/g;
(c) the pore volume with respect to pores each having a radius of from 10 to 100 Å is from 0.5 to 2.0 cm³/g; and
(d) the specific surface area is from 800 to less than 2000 m²/g.

13. The method according to item 12 above, wherein the active metal species further comprises at least one metal selected from the group consisting of rhenium, molybdenum, platinum, palladium, silver and nickel.

14. The method according to item 12 or 13 above, wherein the starting material is at least one compound selected from the group consisting of a dicarboxylic acid represented by the following formula (1):

$$HOOC-R^1-COOH \tag{1}$$

wherein $R^1$ is a $C_2$–$C_{20}$ divalent hydrocarbon group, and a cyclic carboxylic anhydride represented by the following formula (2):

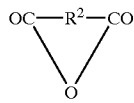
(2)

wherein $R^2$ is a $C_2$–$C_{20}$ divalent hydrocarbon group.

15. The method according to any one of items 12 to 14 above, wherein the starting material is at least one compound selected from the group consisting of succinic acid, glutaric acid, adipic acid, cyclohexane dicarboxylic acid, maleic acid, fumaric acid, terephthalic acid, succinic anhydride and maleic anhydride.

16. The method according to any one of items 12 to 15 above, wherein the starting material is a dicarboxylic acid mixture comprising succinic acid, glutaric acid and adipic acid.

17. The method according to item 16 above, wherein the dicarboxylic acid mixture is derived from a reaction mixture obtained by subjecting at least one compound selected from the group consisting of cyclohexanone and cyclohexanol to oxidation reaction.

18. The method according to any one of items 12 to 17 above, wherein the catalytic hydrogenation is conducted under conditions wherein the temperature is from 100 to 300° C. and the hydrogen pressure is from 1 to 25 MPa.

The present invention will now be described in detail.

The catalyst of the present invention for hydrogenating a carboxylic acid is a catalyst comprising an activated carbon having carried thereon an active metal species comprising ruthenium and tin, wherein the activated carbon is produced by subjecting a carbonaceous material to activation treatment using zinc chloride, followed by calcination.

In general, for the production of an activated carbon, an activation step for imparting adsorptive properties is necessary. The method for the activation can be roughly classified into two methods.

One of the two methods is a so-called "gas activation method", which is a method in which a carbonaceous material is subjected to activation treatment using an oxidative gas, such as steam, carbon dioxide or air. At present, in the production of an activated carbon, the activation treatment is performed mainly by the gas activation method. The gas activation method is most widely, frequently employed in the countries around the world, including the U.S.A.

The other of the two methods is a so-called "chemical activation method", which is a method in which a carbonaceous material is subjected to activation treatment using a salt or acid having a dehydrating activity, such as calcium chloride, magnesium chloride, zinc chloride, phosphoric acid, sulfuric acid or an alkali, e.g., sodium hydroxide or potassium hydroxide. At present, the chemical activation method is used only for the production of an activated carbon for use in special application fields.

The properties of an activated carbon, especially the pore distribution of the activated carbon (i.e., the relationship between the radii of the pores of the activated carbon and the pore volumes of the pores having the radii), vary depending on the activation method employed.

For example, in the most generally employed method for producing an activated carbon, an activation method is used which comprises subjecting a carbonaceous material to steam treatment. In the activated carbon produced using this activation method (i.e., steam-activated carbon), the ratio of pores having large radii is small. That is, the steam-activated carbon has a pore volume as small as from 0.02 to 0.4 cm³ with respect to pores having a radius in the range of from 10 to 100 Å (such pores are called "transitional pores", which are in contrast to micropores which are pores each having a radius of less than 10 Å and in contrast to macropores which are pores each having a radius of more than 100 Å).

On the other hand, an activated carbon produced by a method which comprises subjecting a carbonaceous material to activation treatment using zinc chloride, followed by calcination (i.e., zinc chloride-activated carbon) exhibits an especially large pore volume with respect to the transitional pores, as compared to that of other activated carbons.

The catalyst of the present invention for hydrogenating a carboxylic acid is obtained using a zinc chloride-activated carbon. The catalyst of the present invention is obtained by causing the below-described active metal species to be carried on a zinc chloride-activated carbon. No catalyst for hydrogenating a carboxylic acid is known wherein the catalyst is produced using a zinc chloride-activated carbon as a carrier.

A zinc chloride-activated carbon can be produced by the conventional method. With respect to the details of the method for producing a zinc chloride-activated carbon, reference can be made to the following two documents:

1) "Kasseitan Dokuhon Dainihan (Reference Book on Activated Carbons, Second Edition)" (edited by Hiroshi YANAI, written by Nobuo ISHIZAKI, published by The Nikkan Kogyo Shimbun Ltd., Japan (1996)); and
2) "Shinpan Kasseitan (New Edition, Activated Carbons)" (written by Yuuzou SANADA et al., published by Kodansha Ltd., Japan (1992)).

As described in these documents, a zinc chloride-activated carbon can be produced by a method comprising impregnating a carbonaceous material (such as sawdust, a peat having a low ash content, a wheat straw, a ditch reed, a nut or a nutshell) with a concentrated aqueous zinc chloride solution, followed by calcination. Specifically, a zinc chloride-activated carbon can be produced by the following method. A carbonaceous material is impregnated with an aqueous zinc chloride solution having a specific gravity of approximately 1.8, wherein the aqueous solution is used in an amount which is 0.5 to 4.0 times the weight of the carbonaceous material, and the resultant zinc chloride solution-impregnated carbonaceous material is calcined at a temperature of from 550 to 750° C. in an atmosphere of an inert gas. The resultant calcined product is washed first with hydrochloric acid and then with water to thereby remove most of the zinc chloride. If desired, after the activation treatment using zinc chloride, a further activation treatment using a gas, such as steam, may be conducted. Also, for removing impurities, before the activated carbon has carried thereon the active metal species described below, the activated carbon may be treated with hot water.

In a preferred mode according to another aspect of the present invention, it is required that the activated carbon, prior to having carried thereon the active metal species, exhibit the following properties (a) to (d):

(a) the total pore volume is from 1.2 to 3.0 cm$^3$/g;
(b) the pore volume with respect to pores each having a radius of less than 10 Å is from 0.03 to 0.8 cm$^3$/g;
(c) the pore volume with respect to pores each having a radius of from 10 Å to 100 Å is from 0.5 to 2.0 cm$^3$/g; and
(d) the specific surface area is from 800 to less than 2,000 m$^2$/g.

By virtue of the above-mentioned property (c) of the activated carbon which is used as a carrier in the present invention (i.e., the property that the activated carbon exhibits an especially large pore volume with respect to the transitional pores), the catalyst of the present invention can be advantageously used for the hydrogenation of a wide variety of carboxylic acids, especially dicarboxylic acids.

The reason why the activated carbon exhibiting the property (c) mentioned above is effective as a carrier for a catalyst for performing the hydrogenation of a wide variety of carboxylic acids, such as dicarboxylic acids, has not yet been elucidated. However, the reason is presumed to reside in that since, in the case of the zinc chloride-activated carbon, the pore volume with respect to the transitional pores is large (i.e., the ratio of the transitional pores is high), as compared to the case of a gas-activated carbon, such as a steam-activated carbon, the catalyst of the present invention can exhibit an effect that, during the hydrogenation reaction, a carboxylic acid and hydrogen gas can be rapidly diffused into the pores of the catalyst, so that the hydrogenation of the carboxylic acid in the pores of the catalyst can efficiently proceed (for example, in the case where a dicarboxylic acid is used as a raw material, those which can be rapidly diffused into the pores of the catalyst are a dicarboxylic acid, a hydroxycarboxylic acid (reaction intermediate) and hydrogen gas).

On the other hand, for the catalyst of the present invention to have a strength sufficient to maintain its morphology, it is necessary that the activated carbon used in the present invention exhibit the properties (a), (c) and (d) mentioned above.

For imparting a higher strength to the catalyst of the present invention while maintaining its applicability to the hydrogenation of a wide variety of carboxylic acids, it is preferred that the activated carbon, prior to having carried thereon the active metal species, exhibits the following properties (e) to (h):

(e) the total pore volume of from 1.4 to 2.7 cm$^3$/g;
(f) the pore volume with respect to pores each having a radius of less than 10 Å is from 0.04 to 0.7 cm$^3$/g;
(g) the pore volume with respect to pores each having a radius of from 10 to 100 Å is from 0.7 to 1.8 cm$^3$/g; and
(h) the specific surface area is from 1000 to less than 1800 m$^2$/g.

In the present invention, the pore volume (the total pore volume, the pore volume with respect to pores each having a radius of less than 10 Å and the pore volume with respect to pores each having a radius of from 10 to 100 Å) and the specific surface area are determined by the nitrogen adsorption method, using the Brunauer-Emmett-Teller (BET) adsorption isotherm.

It is known that the pores which can be measured by the nitrogen adsorption method are pores each having a radius of from approximately 8 Å to approximately 500 Å. Therefore, in the present invention, the term "pores each having a radius of less than 10 Å" means "pores each having a radius of from approximately 8 Å to less than 10 Å". Further, in the present invention, the term "the total pore volume" means "the pore volume with respect to pores each having a radius of from approximately 8 Å to approximately 500 Å". Some measuring apparatuses based on the nitrogen adsorption method can give data, taking into consideration pores each having a radius falling outside of the above-mentioned range. However, even in such case, pores each having a radius of less than approximately 8 Å and pores each having a radius of more than approximately 500 Å cannot be measured by the nitrogen adsorption method.

With respect to the measurement of the above-mentioned properties of an activated carbon, the measured values may vary depending on the measuring apparatus employed. In the present invention, the above-mentioned properties of an activated carbon are measured using ASAP-2400 type BET multi-point pore distribution measuring apparatus (manufactured and sold by Micromeritics Instrument Corporation, U.S.A.).

In the present invention, with respect to the morphology of the activated carbon, there is no particular limitation. Therefore, the activated carbon may be in a powder form or in a molded form having, e.g., a granular, cylindrical, spherical or pellet shape, wherein the activated carbon in a molded form can be obtained by molding a mixture of an activated carbon in a powder form and an appropriate additive (such as a binder).

The use of an activated carbon in a powder form is preferred when an agitation type mixing vessel is used as a reactor in the production of a primary alcohol by using the catalyst of the present invention. The use of an activated carbon in a molded form is preferred when a fixed-bed reactor is used as a reactor in the production of a primary alcohol by using the catalyst of the present invention.

With respect to the activated carbon in a powder form, the average particle diameter thereof is preferably from 0.5 to 100 $\mu$m.

With respect to the activated carbon in a granular molded form, the average diameter thereof is preferably from approximately 1 to 5 mm.

With respect to the activated carbon in a cylindrical molded form, the average diameter thereof is preferably from approximately 1 to 5 mm, and the average length thereof is preferably from approximately 5 mm to 3 cm.

With respect to the activated carbon in a spherical molded form, the average diameter thereof is preferably from approximately 1 mm to 1 cm.

With respect to the pelletized activated carbon, the average diameter thereof is preferably from approximately 5 mm to 1 cm, and the average thickness thereof is preferably from approximately 1 mm to 1 cm.

The catalyst of the present invention for hydrogenating a carboxylic acid is obtained by causing an active metal species comprising ruthenium and tin to be carried on the above-mentioned zinc chloride-activated carbon.

It is preferred that, in addition to ruthenium and tin, the above-mentioned active metal species further comprises at least one metal selected from the group consisting of rhenium, molybdenum, platinum, palladium, silver and nickel, more advantageously rhenium, molybdenum or platinum, especially advantageously rhenium.

In the present invention, it is preferred that each of the amounts of ruthenium and tin carried on the activated carbon is independently from 0.5 to 50% by weight, more advantageously from 1 to 10% by weight, based on the weight of the carrier. It is preferred that the atomic ratio of ruthenium to tin (ruthenium: tin) is from 1:0.1 to 1:2, more advantageously from 1:0.2 to 1:1.3.

When the above-mentioned active metal species (comprising ruthenium and tin) further comprises at least one metal selected from the group consisting of rhenium, molybdenum, palladium, silver and nickel, the amount of the at least one metal is preferably from 0.1 to 5, more preferably from 0.2 to 2, in terms of the atomic ratio thereof to ruthenium.

When the above-mentioned active metal species (comprising ruthenium and tin) further comprises platinum, the amount of platinum is preferably from 0.01 to 5, more preferably from 0.1 to 2, in terms of the atomic ratio thereof to ruthenium.

As a method for causing the active metal species to be carried on an activated carbon, there can be used any of the conventional methods generally used for producing a catalyst comprising a carrier having carried thereon a catalyst component. Examples of such conventional methods include a dipping method, an ion exchange method and an impregnation method.

When the active metal species is caused to be carried on an activated carbon by the dipping method, compounds containing the metals used as an active metal species (hereinafter, each compound is referred to as a "metal compound") are dissolved in a solvent (such as water) to thereby prepare a metal compound solution, and an activated carbon is dipped in the solution to thereby cause the metal compounds to be carried on the carrier. The resultant activated carbon having carried thereon the metal compounds is subjected to drying, followed by reduction treatment, to thereby obtain the catalyst of the present invention. If desired, after the drying and before the reduction treatment, the activated carbon having carried thereon the metal compounds may be calcined.

The type of the above-mentioned metal compound used in the production of the catalyst may vary depending on the method for producing the catalyst. Representative examples of metal compounds include an inorganic acid salt, such as a nitrate, a sulfate, and a chloride; an organic acid salt, such as an acetate; a hydroxide; an oxide; and an organometal compound. A water-soluble compound is especially preferred.

Examples of metal compounds containing ruthenium include ruthenium chloride, ruthenium nitrate, acetylacetonatoruthenium, ruthenium carbonyl and the like. Of these compounds, ruthenium chloride is preferred.

Examples of metal compounds containing tin include tin(II) chloride, sodium stannate, tin(II) acetate and the like. Of these compounds, tin(II) chloride and tin(II) acetate are preferred.

Examples of metal compounds containing rhenium include dirhenium(VII) heptaoxide, perrhenic acid (an aqueous solution of dirhenium(VII) heptaoxide) and the like. Of these compounds, perrhenic acid is preferred.

Examples of metal compounds containing platinum include chloroplatinic acid, platinum nitrate, acetylacetonatoplatinum, platinum chloride, platinum bromide, platinum cyanide and the like. Of these compounds, chloroplatinic acid is preferred.

Examples of metal compounds containing molybdenum include hexaammonium heptamolybdate tetrahydrate, molybdenum(II) chloride, ammonium pentachlorooxomolybdate (V) and the like. Of these compounds, hexaammonium heptamolybdate tetrahydrate is preferred.

Examples of metal compounds containing palladium include palladium(II) chloride dihydrate, palladium(II) nitrate, palladium(II) sulfate dihydrate and the like. Of these compounds, palladium(II) nitrate is preferred.

Examples of metal compounds containing silver include silver nitrate, silver perchlorate and the like. Of these compounds, silver nitrate is preferred.

Examples of metal compounds containing nickel include nickel(II) chloride hexahydrate, nickel(II) sulfate, nickel(II) nitrate hexahydrate and the like. Of these compounds, nickel(II) chloride hexahydrate is preferred.

With respect to the concentration of the metal compound solution, there is no particular limitation, and the concentration varies depending on the type of the metal. It is preferred that the concentration of the metal compound solution is approximately from 10 to 20% by weight. With respect to the order in which the metal compounds are caused to be carried on the carrier, there is no particular limitation. All metal compounds may be simultaneously caused to be carried on the carrier, or each metal compound may be separately caused to be carried on the carrier.

The drying of the activated carbon having carried thereon the metal compounds is performed under reduced pressure or under a stream of a dry gas (such as dry nitrogen or dry air), usually at a temperature of less than 100° C.

The reduction treatment of the dried activated carbon (having carried thereon the metal compounds) may be conducted either in a gaseous phase or in a liquid phase.

The gaseous phase reduction can be conducted as follows. The above-mentioned dried activated carbon (having carried thereon the metal compounds) is charged into a vessel and heated to an appropriate temperature. Then, a reducing gas is charged into the vessel or flowed through the vessel. If desired, the reduction operation may be conducted repeatedly.

Examples of reducing gases include hydrogen, a hydrazine vapor and formaldehyde. The reduction temperature is preferably from 150 to 500° C.

The liquid phase reduction can be conducted as follows. The above-mentioned dried activated carbon (having carried thereon the metal compounds) is suspended in an appropriate solvent and then treated with an appropriate reducing agent at a temperature of from room temperature to 250° C. under a pressure of from atmospheric pressure to 20 MPa.

Examples of reducing agents include sodium borohydride, lithium aluminum hydride and diethylzinc. Further, the above-mentioned reducing gases used for the gaseous phase reduction may be used for the liquid phase reduction.

With respect to the solvent used for the liquid phase reduction, there is no particular limitation. Examples of solvents include water; alcohols, such as methanol and ethanol; and hydrocarbons, such as hexane, benzene and naphthalene. However, when a reducing agent which is reactive with water and an alcohol (such as lithium aluminum hydride and diethylzinc) is used, a compound which is not water and has no hydroxyl group, such as a hydrocarbon (e.g., hexane, benzene or naphthalene), is used as a solvent.

The calcination of the dried activated carbon (which is optional) is conducted prior to the reduction treatment, usually at a temperature of from 100 to 600° C. under a stream of nitrogen or air.

With respect to the morphology of the catalyst of the present invention, there is no particular limitation. The catalyst of the present invention may have any morphology resulting from the morphology of the activated carbon used as a carrier.

It is preferred that the morphology of the catalyst of the present invention is appropriately selected in accordance with the mode of the hydrogenation reaction using the catalyst of the present invention.

For example, when an agitation type mixing vessel is used as a reactor in the production of a primary alcohol by using the catalyst of the present invention, it is preferred that the catalyst is produced using an activated carbon in a powder form, which has an average particle diameter of from 0.2 to 200 $\mu$m, more advantageously from 0.5 to 100 $\mu$m. The reason why this particle diameter is preferred is because, when the particle diameter of the catalyst is too large, the particles of the catalyst are gradually broken by the agitation during the hydrogenation reaction, so that the yield of the desired primary alcohol fluctuates.

On the other hand, when a fixed-bed reactor is used as a reactor in the production of a primary alcohol by using the catalyst of the present invention, it is preferred that the catalyst is produced using an activated carbon in a molded form having, e.g., a granular, cylindrical, spherical or pallet shape, wherein the activated carbon in a molded form has a diameter of from 1 mm to 1 cm, more advantageously from 2 mm to 5 mm. The reason why this diameter of the catalyst is preferred is because, when the diameter of the catalyst is too small, the pressure loss in the hydrogenation reaction becomes large, so that it becomes difficult to supply the below-described starting material, reaction solvent (water) and hydrogen gas.

Using the thus obtained catalyst, a primary alcohol can be produced from a carboxylic acid. Hereinbelow, an explanation is made with respect to the method for producing a primary alcohol from a carboxylic acid using the catalyst of the present invention.

In the present invention, a primary alcohol is produced by a method which comprises reacting at least one starting material selected from the group consisting of a carboxylic acid and a carboxylic anhydride with hydrogen gas in the presence of water and the catalyst to thereby effect a hydrogenation of the starting material.

Examples of carboxylic acids which can be used as the stating material include saturated aliphatic mono-carboxylic acids, such as formic acid, acetic acid, propionic acid, butyric acid, valeric acid, capronic acid, pentanoic acid, caprylic acid and pelargonic acid; saturated aliphatic dicarboxylic acids, such as oxalic acid, malonic acid, succinic acid, glutaric acid, adipic acid, pimeric acid, suberic acid, azelaic acid, sebacic acid, methylsuccinic acid, 2,2-dimethylsuccinic acid, 2,3-dimethylsuccinic acid, methylmalonic acid, $\alpha$-methylglutaric acid, $\beta$-methylglutaric acid, 2,2-dimethylglutaric acid, 2,4-dimethylglutaric acid, 3,3-dimethylglutaric acid, 2-ethyl-2-methylsuccinic acid, 2,2,5,5-tetramethylhexanedioic acid and 3-methyladipic acid; unsaturated aliphatic monocarboxylic acids, such as acrylic acid, crotonic acid, isocrotonic acid, vinylacetic acid, and methacrylic acid; unsaturated aliphatic dicarboxylic acids, such as fumaric acid, maleic acid, methylmaleic acid, methylfumaric acid, itaconic acid, citraconic acid, mesaconic acid, glutaconic acid, muconic acid, 2-methylmuconic acid, acetylenedicarboxylic acid, and 1-propyn-1,3-dicarboxylic acid; aliphatic polycarboxylic acids, such as methanetricarboxylic acid and ethylenetricarboxylic acid; alicyclic monocarboxylic acids, such as cyclohexanecarboxylic acid, cholanoic acid, lithocholic acid and cholic acid; alicyclic dicarboxylic acids, such as 1,2-cyclohexanedicarboxylic acid, 1,3-cyclohexanedicarboxylic acid, 1,4-cyclohexanedicarboxylic acid and 3,3-tetramethyleneglutaric acid; and aromatic carboxylic acids, such as benzoic acid, toluic acid, cumic acid, phthalic acid, isophthalic acid and terephthalic acid. These carboxylic acids may be used individually or in combination.

Further, in the method of the present invention, a carboxylic anhydride can also be used as the starting material. As described below, in the method of the present invention, the hydrogenation is conducted in the presence of water, preferably while heating. Under such conditions, a carboxylic anhydride is hydrolyzed to become a corresponding carboxylic acid. Therefore, in the method of the present invention, even when a carboxylic anhydride is used as the starting material, the production of a primary alcohol can be conducted in the same manner as in the case where a carboxylic acid is used as the starting material.

Examples of carboxylic anhydrides which can be used as the stating material in the present invention include acetic anhydride, propionic anhydride, butyric anhydride, succinic anhydride, glutaric anhydride, adipic anhydride, polyadipic anhydride, maleic anhydride, methylmaleic anhydride, benzoic anhydride and phthalic anhydride. These carboxylic anhydrides may be used individually or in combination.

In the present invention, the production of a primary alcohol can be conducted either by using the above-mentioned carboxylic anhydride alone or by using the above-mentioned carboxylic acid and the carboxylic anhydride in combination.

Further, in the method of the present invention, when an unsaturated carboxylic acid (or a corresponding carboxylic anhydride) is used as the starting material, a saturated alcohol is obtained by the hydrogenation of the starting material which is conducted in the presence of the catalyst of the present invention. On the other hand, when an aromatic carboxylic acid (or a corresponding carboxylic anhydride) is used as the starting material, an alicyclic alcohol is obtained by performing the hydrogenation of the starting material in the presence of the catalyst of the present invention.

The above-mentioned carboxylic acids and carboxylic anhydrides may have various substituents. However, needless to say, depending on the type of the substituent, it is possible that the structure of the substituent changes under the influence of the catalyst of the present invention. For example, a nitro group is reduced to become an amino group.

In the method of the present invention, it is preferred that the above-mentioned carboxylic acid and carboxylic anhydride do not contain any hetero atoms, such as a nitrogen atom, a sulfur atom and a phosphorus atom. The reason for this is because there is a possibility that a compound containing any of the above-mentioned hetero atoms acts as a catalyst poison to de-activate the catalyst of the present invention.

In the method of the present invention, it is preferred that the starting material is at least one compound selected from the group consisting of a dicarboxylic acid represented by the following formula (1):

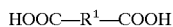

$$\text{HOOC—R}^1\text{—COOH} \quad (1)$$

wherein $R^1$ is a $C_2$–$C_{20}$ divalent hydrocarbon group, and a cyclic carboxylic anhydride represented by the following formula (2):

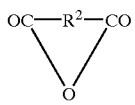

(2)

wherein $R^2$ is a $C_2$–$C_{20}$ divalent hydrocarbon group.

Examples of dicarboxylic acids represented by formula (1) above include succinic acid, glutaric acid, adipic acid, cyclohexanedicarboxylic acid, maleic acid, fumaric acid, and terephthalic acid. Examples of cyclic carboxylic anhydrides represented by formula (2) above include succinic anhydride and maleic anhydride.

With respect to the above-exemplified starting materials, most of them are commercially available and can be obtained relatively easily. In the present invention, it is also possible to use, as the starting material, waste products of various chemical processes, which contain a large amount of a carboxylic acid or a carboxylic anhydride. Such waste products as such may be used as the starting material or, alternatively, may be subjected to appropriate treatment prior to use.

For example, in the production of adipic acid, which is conducted by subjecting at least one compound selected from the group consisting of cyclohexanone and cyclohexanol to oxidation reaction with an oxidizing agent (mainly, nitric acid), considerable amounts of succinic acid and gutaric acid are by-produced during the oxidation reaction. From the resultant oxidation reaction mixture, most of the adipic acid produced (desired compound) is recovered by crystallization. The mother liquor obtained in the crystallization contains succinic acid and glutaric acid as well as adipic acid which has not been able to be recovered. Generally, the mother liquor is disposed as a waste product. However, in the present invention, the above-mentioned dicarboxylic acid mixture obtained as the mother liquor containing succinic acid, glutaric acid and adipic acid can be used as the starting material.

With respect to the above-mentioned mother liquor obtained in the crystallization, this mother liquor as such can be used as a dicarboxylic acid mixture. However, when the mother liquor as such is used as a dicarboxylic acid mixture, it is possible that the catalytic activity is lowered under the influence of the oxidizing agent (mainly, nitric acid) remaining in the mother liquor, thereby lowering the yield of diol which is a desired compound. Therefore, it is preferred that the mother liquor is subjected to appropriate treatment, such as removal of the oxidizing agent (e.g. nitric acid), and the resultant treated mother liquor is used as a dicarboxylic acid mixture.

The catalyst used in the method of the present invention is applicable to the hydrogenation of a wide variety of carboxylic acids. Therefore, when the above-mentioned dicarboxylic acid mixture is used as the starting material, succinic acid, glutaric acid and adipic acid contained in the mixture are converted into 1,4-butanediol, 1,5-pentanediol and 1,6-hexanediol, respectively. These diols can be separated and purified by a conventioal method, such as distillation.

Each of 1,4-butanediol, 1,5-pentanediol and 1,6-hexanediol is a commercially very important compound which is used as a raw material for producing various resins, and the like. Therefore, the above-mentioned dicarboxylic acid mixture is especially preferred as a starting material, because the above-mentioned important compounds can be obtained.

As is apparent from the above, the method of the present invention is extremely advantageous not only in that a waste product formed in the production of adipic acid (wherein the waste product is derived from a reaction mixture obtained by subjecting at least one compound selected from the group consisting of cyclohexanone and cyclohexanol to oxidation) can be utilized, but also in that various commercially important compounds, such as 1,4-butanediol, 1,5-pentanediol and 1,6-hexanediol, can be simultaneously produced from the waste product.

In the method of the present invention, the above-mentioned starting material is reacted with hydrogen gas in the presence of water and the above-mentioned catalyst to thereby effect a hydrogenation of the starting material.

Generally, the water as a solvent is used in the liquid state; however, the water need not be in the liquid state when the hydrogenation is effected in the gaseous phase.

When water is used as a solvent, water can be used in combination with a solvent other than water. The other solvent may be either a water-soluble solvent or a water-insoluble solvent. Further, it is preferred that the other solvent is not reduced by the action of the catalyst.

Preferred examples of solvents used in combination with water include alcohols, such as methanol and ethanol;

ethers, such as tetrahydrofuran and dioxane; and saturated hydrocarbons, such as hexane and cyclohexane.

When the hydrogenation is effected in the absence of water, a disadvantage is caused wherein, especially when a carboxylic acid is used as the starting material, the hydrogenation reaction hardly proceeds. The reason for this has not yet been elucidated, but is considered to be as follows.

In the case of the hydrogenation conducted in the presence of water and a water-insoluble catalyst, it is considered that the starting material and hydrogen gas are adsorbed on the surface of the catalyst and, then, the hydrogenation proceeds on the surface of the catalyst. On the other hand, when the hydrogenation is conducted in the presence of a water-insoluble catalyst and in the absence of water, the starting material (especially, a carboxylic acid) is too strongly adsorbed on the surface of the catalyst, so that hydrogen gas cannot have access to the surface of the catalyst and, hence, a reaction does not occur on the surface of the catalyst.

Further, when the hydrogenation is effected in the absence of water, another disadvantage is also caused wherein, especially when a carboxylic acid is used as the starting material, a deterioration of the catalyst is accelerated.

Further, when the hydrogenation of a dicarboxylic acid as the starting material is effected in the absence of water, still another disadvantage is caused wherein the yield of the primary alcohol is lowered. The reason for this is because, when the hydrogenation of a dicarboxylic acid is effected in the absence of water, a lactone is produced from a hydroxycarboxylic acid (which is an intermediate product) and the lactone produced forms a cyclic ether as a by-product.

The amount of water used as a solvent is not particularly limited; however it is preferred to use water in an amount sufficient to dissolve therein the whole of the stating material at a temperature employed for effecting the hydrogenation. Generally, water as a solvent is used in an amount of 0.5 to 100 parts by weight, preferably 1 to 20 parts by weight per part by weight of the starting material.

In the method of the present invention, the amount of the catalyst used is not particularly limited; however, the amount is preferably from 0.1 to 50% by weight, more preferably from 1 to 30% by weight, based on the weight of the starting material, i.e., the carboxylic acid and/or the carboxylic anhydride.

With respect to the conditions for the above-mentioned hydrogenation, it is preferred that the hydrogenation is conducted under conditions wherein the temperature is from 100 to 300° C., more advantageously from 130 to 250° C., and the hydrogen pressure is from 1 to 25 MPa, more advantageously from 10 to 20 MPa.

The hydrogenation can be conducted in either the gaseous phase or the liquid phase by appropriately selecting the reaction conditions and the type of the starting material. However, the hydrogenation is generally conducted in the liquid phase. Further, the hydrogenation can be conducted in either a continuous manner or a batchwise manner.

In the method of the present invention, a reactor used for the hydrogenation is not particularly limited, and any of various conventional reactors can be used. For example, a agitation type mixing vessel can be used for conducting a suspension reaction. Alternatively, a fixed-bed reactor can be used for conducting a fixed-bed flow reaction.

In the method of the present invention, it is preferred that the conversion of the starting material is high. The conversion is preferably 90% or more, more preferably 97% or more. When a large amount of a carboxylic acid (which has remained unreacted or is derived from a carboxylic anhydride) is present in the reaction mixture obtained by the method of the present invention, the carboxylic acid reacts with the desired primary alcohol to form an ester, so that a lowering of the yield of the primary alcohol occurs.

On the other hand, when the hydrogenation is continued for a long time after the conversion of the carboxylic acid into a primary alcohol by hydrogenation has been substantially completed, it is possible that the yield of the primary alcohol is lowered by hydrogenolysis of the primary alcohol.

In the method of the present invention, it is preferred that, for maximizing the yield of the primary alcohol, the hydrogenation conditions are appropriately selected, taking into consideration the above-mentioned factors which lead to a lowering of the yield of the primary alcohol.

In the method of the present invention, the reaction time is not particularly limited, and can be appropriately selected so that substantially all carboxylic acid (used as the starting material or derived from the carboxylic anhydride used as the starting material) is converted and the yield of the desired primary alcohol becomes as high as possible. Such an appropriate reaction time varies depending on the reaction conditions, such as the temperature and the hydrogen pressure; however, the reaction time is generally from 1 to 50 hours. For example, when the hydrogenation is conducted under the above-mentioned preferred conditions wherein the temperature is from 130 to 250° C. and the hydrogen pressure is from 10 to 20 MPa, the reaction time is generally from 3 to 20 hours.

When the reaction time is too long, the desired primary alcohol produced undergoes hydrogenolysis to form a corresponding alkane, depending on the reaction temperature, so that a lowering of the yield of the primary alcohol disadvantageously occurs.

The optimum reaction time can be determined by a method in which the determination of the yield of the primary alcohol (wherein the determination is conducted by sampling and analyzing a part of the reaction mixture obtained by the hydrogenation) is conducted at predetermined points in time during the hydrogenation to determine the reaction time at which the yield of the primary alcohol is maximized.

When a primary alcohol is produced by the method of the present invention, it is possible that various by-products are formed depending on the type of the starting material and the reaction conditions. For example, when a monocarboxylic acid (and/or a corresponding carboxylic anhydride) is used as the starting material, it is possible that the hydrogenation is accompanied by the formation of the following by-products:

an alkane formed by the hydrogenolysis of the desired primary alcohol (wherein the number of carbon atoms of the alkane is the same as that of the desired primary alcohol), and an alkane formed by the decarboxylation of the starting material, i.e., a carboxylic acid and/or a carboxylic anhydride (wherein the number of carbon atoms of the alkane is smaller than that of the desired primary alcohol).

On the other hand, when a dicarboxylic acid (or a corresponding cyclic dicarboxylic anhydride) is used as the starting material, it is possible that the hydrogenation is accompanied by the formation of the following by-products:

a hydroxycarboxylic acid formed by the reduction of one of the two carboxyl groups of the dicarboxylic acid, a lactone formed by the cyclodehydration of the above-mentioned hydroxycarboxylic acid, a cyclic ether formed by the reduction of the above-mentioned lactone or by the cyclodehydration of the desired diol, and a monohydric alcohol formed by the partial hydrogenolysis of the desired diol.

These by-products can be easily removed by any of the conventional methods, such as distillation, fractional recrystallization and chromatography.

BEST MODE FOR CARRYING OUT THE INVENTION

Hereinbelow, the present invention will be described in more detail with reference to the following Examples, Comparative Examples and Reference Example; however, they should not be construed as limiting the scope of the present invention.

In the following Examples, Comparative Examples and Reference Example, various properties were measured and analyzed by the following methods.

(1) Pore Distribution and Specific Surface Area of an Activated Carbon

The total pore volume, the pore volume with respect to pores each having a radius of less than 10 Å, the pore volume with respect to pores each having a radius of from 10 to 100 Å and the specific surface area were measured by the nitrogen adsorption method, using an ASAP-2400 type BET multi-point pore distribution measuring apparatus (manufactured and sold by Micromeritics, U.S.A.).

The data processing for calculating the pore volume was performed by the Barrett-Joyner-Halenda method (BJH method). The details of the BJH method is described in "Shokubai Koza Dai-3-kan (Kisohen 3). Kotai-shokubai no Kyarakutarizeishon (Lecture on Catalysts Vol. 3 (Fundamental Section 3) Characterization of Solid Catalyst)" (edited by the Japan Catalyst Society and published by Kodansha Ltd., Japan, 1985).

(2) Conversion of a Starting Material

A reaction mixture obtained by hydrogenating a starting material was diluted with distilled water so that the weight of the resultant diluted mixture became approximately 10 times as large as the weight of the starting material. To the obtained diluted mixture was added pimelic acid as an internal standard (in an amount of about 0.1 part by weight, relative to 1 part by weight of the diluted mixture), thereby obtaining a sample solution.

This sample solution was analyzed by high performance liquid chromatography (HPLC). From the results of the analysis, the conversion is calculated.

Conditions for HPLC

HPLC apparatus: High performance liquid chromatograph Model LC-6A (manufactured and sold by Shimadzu Corp., Japan)

Column: SCR-101H (manufactured and sold by Shimadzu Corp., Japan)

Moving phase: aqueous perchloric acid solution (pH 2.3)

Flow rate: 0.8 ml/min

Detector: differential refractometer (3) Yield of a Primary Alcohol

A reaction mixture obtained by hydrogenating a starting material was diluted with dioxane so that the concentration of the primary alcohol in the resultant diluted mixture became approximately 1% by weight. To the obtained diluted mixture was added diethylene glycol diethyl ether as an internal standard so that the concentration of the internal standard in the resultant became approximately 1% by weight, thereby obtaining a sample solution.

This sample solution was analyzed by gas chromatography (GC). From the results of the analysis, the yield of the primary alcohol is calculated.

Conditions for GC

Column: DB-WAX (column length: 30 m, inner diameter: 0.25 mm, film thickness: 0.25 μm), manufactured and sold by J & W Scientific, U.S.A.

GC apparatus: gas chromatograph Model GC-14B, manufactured and sold by Shimadzu Corporation, Japan Carrier gas: helium Detector: flame ionization detector (FID)

REFERENCE EXAMPLE 1

Preparation of a Dicarboxylic Acid Mixture 8.35 g of copper (metal) and 1.20 g of vanadium pentoxide were added to and dissolved in 1,670 g of 60 wt % aqueous nitric acid, and the resultant solution was charged into a glass flask equipped with a stirrer, a dropping funnel, a condenser tube and a thermometer. To this solution was added 250 g of cyclohexanol (which was obtained by purifying a commercially available product by distillation) over 2 hours under water cooling while maintaining the temperature of the solution in the glass flask at 80° C. or less. After the addition of the cyclohexanol, the resultant mixture in the glass flask was stirred at 80° C. for an hour to thereby obtain a reaction mixture. The obtained reaction mixture was cooled down to room temperature to precipitate crude adipic acid, and the precipitated crude adipic acid was separated from the mother liquor by filtration.

The obtained crude adipic acid was dissolved in 450 g of ion-exchanged water at 90° C., and the resultant solution was cooled down slowly to room temperature to thereby precipitate the adipic acid. The precipitated adipic acid was separated from the mother liquor by filtration.

The above-described procedure for the synthesis of adipic acid was further repeated 5 times, and all mother liquors obtained by 6 runs of the procedure for the synthesis of adipic acid were mixed together to obtain a mother liquor mixture. 5,000 g of the obtained mother liquor mixture was heated at about 120° C. under atmospheric pressure, thereby distilling off water and most of the nitric acid in the mother liquor mixture, to obtain a residue.

To the obtained residue was added ion-exchanged water in an amount which was 2 times the weight of the residue, to thereby dissolve the residue in the water and obtain an aqueous solution having a water content of 67% by weight. To the obtained aqueous solution was added 100 g of the styrene polymer type cation-exchange resin Amberlite IR-120B (manufactured and sold by ORGANO CORP., Japan; the ion-exchange resin has a sulfonic acid group as a cation-exchange group), and the resultant mixture was stirred gently at room temperature for 2 hours. Then, the Amberlite IR-120 B was removed from the mixture by filtration. By this purification operation, copper and vanadium in the above-mentioned aqueous solution were substantially completely removed.

Subsequently, the thus purified aqueous solution was heated at 120° C. for an hour and then at 170° C. for 15 minutes to distill off water, thereby obtaining a residue. The residue was analyzed by HPLC under the above-mentioned analysis conditions. As a result, it was found that the residue was a dicarboxlyc acid mixture comprised of 23% by weight of succinic acid, 60% by weight of glutaric acid and 17% by weight of adipic acid.

The thus obtained dicarboxlyc acid mixture was used as a starting material in the hydrogenation described below.

EXAMPLE 1

<Preparation of a Catalyst>

2.00 g of ion-exchanged water was charged into a 100 ml eggplant type flask, and then 0.39 g of ruthenium chloride trihydrate and 0.20 g of tin(II) chloride dehydrate were added to and dissolved in the ion-exchanged water in the eggplant type flask. To the resultant solution was added 3.00 g of an activated carbon (grade name "Taikoh SGP", manufactured and sold by Futamura Chemical industries Co. Ltd., Japan), and the resultant mixture was allowed to stand still at room temperature for 15 hours.

Then, the above-mentioned mixture was subjected to evaporation by using an evaporator at 70° C. under 2.7 kPa to distill off water to thereby obtain a residue. Then, the obtained residue was calcined in a nitrogen atmosphere at 150° C. for 2 hours and then subjected to reduction treatment in a hydrogen atmosphere at 450° C. for 2 hours. The resultant product was then cooled down to room temperature in a nitrogen atmosphere and then allowed to stand still in an atmosphere of an (oxygen/nitrogen) gaseous mixture (ratio of oxygen: 0.1% by volume) for 2 hours.

By the method described hereinabove, a catalyst was obtained which comprised an activated carbon having carried thereon 5.0% by weight of ruthenium and 3.5% by weight of tin. (The amount of each metal carried is based on the weight of the activated carbon. This also applies to the description given hereinafter.) Hereinafter, this catalyst is referred to as an "Ru—Sn catalyst".

The above-mentioned activated carbon "Taikoh SGP" has a pore distribution and a specific surface area as shown in the following table.

| | |
|---|---|
| Total pore volume: | 2.02 cm$^3$/g |
| Pore volume with respect to pores each having a radius of less than 10 Å: | 0.52 cm$^3$/g |
| Pore volume with respect to pores each having a radius of from 10 to 100 Å: | 1.02 cm$^3$/g |
| Specific surface area: | 1786 m$^2$/g |

On the other hand, when the pore distribution and specific surface area of the above-mentioned activated carbon were measured by the nitrogen adsorption method using the BET multi-point pore distribution measuring apparatus Sorptmatic 1800 (manufactured and sold by Caro Erba, Italy), the results shown in the table below were obtained.

| | |
|---|---|
| Total pore volume: | 1.08 cm$^3$/g |
| Pore volume with respect to pores each having a radius of less than 10 Å: | 0.05 cm$^3$/g |
| Pore volume with respect to pores each having a radius of from 10 to 100 Å: | 0.75 cm$^3$/g |
| Specific surface area: | 1050 m$^2$/g |

The data processing for calculating the pore volume was performed by the Cranston-Inkley method (CI method). The details of the CI method are described in "Advance in Catalysis" 9, 143 (written by R. W. Cranston and F. A. Inkley, published by Academic Press (1957)).

As apparent from the above, the measured values of the pore distribution and specific surface area of an activated carbon can greatly vary depending on the measuring apparatus employed.

<Hydrogenation Reaction of a Dicarboxylic Acid Mixture>

5 g of ion-exchanged water, 2.1 g of the dicarboxylic acid mixture obtained in Reference Example 1 and 0.15 g of the Ru—Sn catalyst mentioned above were charged into a 30 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 15 MPa, and then hydrogenation was performed at the above-mentioned temperature under the above-mentioned hydrogen gas pressure for 10 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversions of succinic acid, glutaric acid and adipic acid were 87%, 87% and 90%, respectively, and the yields of 1,4-butanediol, 1,5-pentanediol and 1,6-hexanediol were 43%, 69% and 50%, respectively.

EXAMPLE 2

<Preparation of a Catalyst>

2.00 g of ion-exchanged water was charged into a 100 ml eggplant type flask, and then 0.39 g of ruthenium chloride trihydrate, 0.20 g of tin(II) chloride dihydrate and 0.22 g of dirhenium heptaoxide were added to and dissolved in the ion-exchanged water in the eggplant type flask. To the resultant solution was added 3.00 g of the same activated carbon as used in Example 1, and the resultant mixture was allowed to stand still at room temperature for 15 hours.

Then, the above-mentioned mixture was subjected to evaporation by using an evaporator at 70° C. under 2.7 kPa to distill off water to thereby obtain a residue. Then, the obtained residue was calcined in a nitrogen atmosphere at 150° C. for 2 hours and then subjected to reduction treatment in a hydrogen atmosphere at 450° C. for 2 hours. The resultant product was then cooled down to room temperature in a nitrogen atmosphere and then allowed to stand still in an atmosphere of an (oxygen/nitrogen) gaseous mixture (ratio of oxygen: 0.1% by volume) for 2 hours.

By the method described hereinabove, a catalyst was obtained which comprised an activated carbon having carried thereon 5.0% by weight of ruthenium, 3.5% by weight of tin and 5.6% by weight of rhenium. Hereinafter, this catalyst is referred to as an "Ru—Sn—Re catalyst".

<Hydrogenation Reaction of a Dicarboxylic Acid Mixture>

Substantially the same procedure for hydrogenation reaction as in Example 1 was repeated except that the Ru—Sn—Re catalyst mentioned above was used as a catalyst, to thereby obtain a reaction mixture.

The obtained reaction mixture was analyzed by HPLC and GC under the conditions mentioned above to determine the conversion of the starting material and the yield of the primary alcohol. The analysis showed that the conversions of succinic acid, glutaric acid and adipic acid were 93%, 93% and 97%, respectively, and the yields of 1,4-butanediol, 1,5-pentanediol and 1,6-hexanediol were 53%, 78% and 60%, respectively.

EXAMPLE 3

<Preparation of a Catalyst>

3.36 ml of 5 N hydrochloric acid was charged into a 100 ml eggplant type flask, and then 0.48 g of chloroplatinic acid hexahydrate, 0.84 g of ruthenium chloride trihydrate and 0.51 g of tin(II) chloride dihydrate were added to and dissolved in the 5 N hydrochloric acid in the eggplant type flask. To the resultant solution was added 3.00 g of the same activated carbon as used in Example 1, and the resultant mixture was allowed to stand still at room temperature for 15 hours.

Then, the above-mentioned mixture was subjected to evaporation by using an evaporator at 70° C. under 2.7 kPa to distill off water to thereby obtain a residue. Then, the obtained residue was calcined in a nitrogen atmosphere at 150° C. for 2 hours and then subjected to reduction treatment in a hydrogen atmosphere at 450° C. for 2 hours. The resultant product was then cooled down to room temperature in a nitrogen atmosphere and then allowed to stand still in an atmosphere of an (oxygen/nitrogen) gaseous mixture (ratio of oxygen: 0.1% by volume) for 2 hours.

By the method described hereinabove, a catalyst was obtained which comprised an activated carbon having carried thereon 6.1% by weight of ruthenium, 5.0% by weight of tin and 3.4% by weight of platinum. Hereinafter, this catalyst is referred to as an "Ru—Sn—Pt catalyst".

<Hydrogenation Reaction of a Dicarboxylic Acid Mixture>

Substantially the same procedure for hydrogenation reaction as in Example 1 was repeated except that the Ru—Sn—Pt catalyst mentioned above was used as a catalyst, to thereby obtain a reaction mixture.

The obtained reaction mixture was analyzed by HPLC and GC under the conditions mentioned above to determine the conversion of the starting material and the yield of the primary alcohol. The analysis showed that the conversions of succinic acid, glutaric acid and adipic acid were 94%, 94% and 97%, respectively, and the yields of 1,4-butanediol, 1,5-pentanediol and 1,6-hexanediol were 50%, 76% and 61%, respectively.

EXAMPLE 4

<Preparation of a Catalyst>

Substantially the same procedure for catalyst preparation as in Example 2 was repeated except that 0.08 g of hexaammonium heptamolybdate tetrahydrate was used instead of dirhenium heptaoxide, thereby obtaining a catalyst which comprised an activated carbon having carried thereon 5.0% by weight of ruthenium, 3.5% by weight of tin and 1.5% by weight of molybdenum. Hereinafter, this catalyst is referred to as an "Ru—Sn—Mo catalyst".

<Hydrogenation Reaction of a Dicarboxylic Acid Mixture>

Substantially the same procedure for hydrogenation reaction as in Example 1 was repeated except that the Ru—Sn—Mo catalyst mentioned above was used as a catalyst, to thereby obtain a reaction mixture.

The obtained reaction mixture was analyzed by HPLC and GC under the conditions mentioned above to determine the conversion of the starting material and the yield of the primary alcohol. The analysis showed that the conversions of succinic acid, glutaric acid and adipic acid were 91%, 92% and 95%, respectively, and the yields of 1,4-butanediol, 1,5-pentanediol and 1,6-hexanediol were 57%, 76% and 58%, respectively.

EXAMPLE 5

<Preparation of a Catalyst>

2.06 g of ion-exchanged water was charged into a 100 ml eggplant type flask, and then 0.39 g of ruthenium chloride trihydrate, 0.20 g of tin(II) chloride dihydrate and 0.10 g of palladium nitrate were added to and dissolved in the ion-exchanged water in the eggplant type flask. To the resultant solution was added 3.00 g of the same activated carbon as used in Example 1, and the resultant mixture was allowed to stand still at room temperature for 15 hours.

Then, the above-mentioned mixture was subjected to evaporation by using an evaporator at 70° C. under 2.7 kPa to distill off water to thereby obtain a residue. Then, the obtained residue was calcined in a nitrogen atmosphere at 150° C. for 30 minutes and then subjected to reduction treatment in a hydrogen atmosphere at 500° C. for 2 hours. The resultant product was then cooled down to room temperature in a nitrogen atmosphere and then allowed to stand still in an atmosphere of an (oxygen/nitrogen) gaseous mixture (ratio of oxygen: 0.1% by volume) for 2 hours.

By the method described hereinabove, a catalyst was obtained which comprised an activated carbon having carried thereon 5.0% by weight of ruthenium, 3.5% by weight of tin and 3.2% by weight of palladium. Hereinafter, this catalyst is referred to as an "Ru—Sn—Pd catalyst".

<Hydrogenation Reaction of Succinic Acid>

5 g of ion-exchanged water, 2.10 g of succinic acid and 0.30 g of the Ru—Sn—Pd catalyst mentioned above were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 15 MPa, and then hydrogenation was performed at the above-mentioned temperature under the above-mentioned hydrogen gas pressure for 5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of succinic acid was 97% and the yield of 1,4-butanediol was 53%.

EXAMPLE 6

<Preparation of a Catalyst>

2.00 g of ion-exchanged water was charged into a 100 ml eggplant type flask, and then 0.39 g of ruthenium chloride trihydrate, 0.10 g of tin(II) chloride dihydrate and 0.08 g of silver nitrate were added to and dissolved in the ion-exchanged water in the eggplant type flask. To the resultant solution was added 3.00 g of the same activated carbon as used in Example 1, and the resultant mixture was allowed to stand still at room temperature for 15 hours.

Then, the above-mentioned mixture was subjected to evaporation by using an evaporator at 70 ° C. under 2.7 kPa to distill off water to thereby obtain a residue. Then, the obtained residue was calcined in a nitrogen atmosphere at 150° C. for 30 minutes and then subjected to reduction treatment in a hydrogen atmosphere at 500° C. for 2 hours. The resultant product was then cooled down to room temperature in a nitrogen atmosphere and then allowed to stand still in an atmosphere of an (oxygen/nitrogen) gaseous mixture (ratio of oxygen: 0.1% by volume) for 2 hours.

By the method described hereinabove, a catalyst was obtained which comprised an activated carbon having carried thereon 5.0% by weight of ruthenium, 1.8% by weight of tin and 1.6% by weight of silver. Hereinafter, this catalyst is referred to as an "Ru—Sn—Ag catalyst".

<Hydrogenation Reaction of Succinic Acid>

Substantially the same procedure for hydrogenation reaction as in Example 5 was repeated except that the Ru—Sn—Ag catalyst mentioned above was used as a catalyst instead of the Ru—Sn—Pd catalyst, to thereby obtain a reaction mixture.

The obtained reaction mixture was analyzed by HPLC and GC under the conditions mentioned above to determine the conversion of the starting material and the yield of the primary alcohol. The analysis showed that the conversion of succinic acid was 93% and the yield of 1,4-butanediol was 68%.

EXAMPLE 7

<Preparation of a Catalyst>

1.94 g of ion-exchanged water was charged into a 100 ml eggplant type flask, and then 0.39 g of ruthenium chloride trihydrate, 0.20 g of tin(II) chloride dihydrate and 0.26 g of nickel nitrate were added to and dissolved in the ion-exchanged water in the eggplant type flask. To the resultant solution was added 3.00 g of the same activated carbon as used in Example 1, and the resultant mixture was allowed to stand still at room temperature for 15 hours.

Then, the above-mentioned mixture was subjected to evaporation by using an evaporator at 70° C. under 2.7 kPa to distill off water to thereby obtain a residue. Then, the obtained residue was calcined in a nitrogen atmosphere at 150° C. for 30 minutes and then subjected to reduction treatment in a hydrogen atmosphere at 500° C. for 2 hours. The resultant product was then cooled down to room temperature in a nitrogen atmosphere and then allowed to stand still in an atmosphere of an (oxygen/nitrogen) gaseous mixture (ratio of oxygen: 0.1% by volume) for 2 hours.

By the method described hereinabove, a catalyst was obtained which comprised an activated carbon having carried thereon 5.0% by weight of ruthenium, 3.5% by weight of tin and 1.7% by weight of nickel. Hereinafter, this catalyst is referred to as an "Ru—Sn—Ni catalyst".

<Hydrogenation Reaction of Succinic Acid>

Substantially the same procedure for hydrogenation reaction as in Example 5 was repeated except that the Ru—Sn—Ni catalyst mentioned above was used as a catalyst instead of the Ru—Sn—Pd catalyst, to thereby obtain a reaction mixture.

The obtained reaction mixture was analyzed by HPLC and GC under the conditions mentioned above to determine the conversion of the starting material and the yield of the primary alcohol. The analysis showed that the conversion of succinic acid was 92% and the yield of 1,4-butanediol was 58%.

COMPARATIVE EXAMPLE 1

<Preparation of a Catalyst>

A catalyst was prepared in accordance with the method described in Unexamined Japanese Patent Application Laid-Open Specification No. 10-71332.

Specifically, a catalyst was prepared in the following manner. 50 g of a 30 wt % aqueous nitric acid was added to 20 g of a coal type activated carbon (grade name "DIA-HOPE CX-2", manufactured and sold by Mitsubishi Chemical Corporation, Japan), and the resultant mixture was heated at 95° C. for 3 hours to thereby obtain a reaction mixture. The obtained reaction mixture was subjected to filtration to recover the activated carbon, and the recovered activated carbon was washed 5 times with 400 ml of distilled water, followed by drying at 80° C. under a pressure of approximately 2 mmHg for 12 hours, thereby obtaining a nitric acidtreated carrier.

Substantially the same procedure for catalyst preparation as in Example 2 was repeated except that the above-obtained nitric acid-treated carrier was used as a carrier, thereby obtaining a catalyst which comprised an activated carbon having carried thereon 5.0% by weight of ruthenium, 3.5% by weight of tin and 5.6% by weight of rhenium. Hereinafter, this catalyst is referred to as "comparative catalyst 1".

The above-mentioned activated carbon "DIAHOPE CX-2" has a pore distribution and a specific surface area as shown in the following table.

| | |
|---|---|
| Total pore volume: | 1.07 $cm^3/g$ |
| Pore volume with respect to pores each having a radius of less than 10 Å: | 0.57 $cm^3/g$ |
| Pore volume with respect to pores each having a radius of from 10 to 100 Å: | 0.44 $cm^3/g$ |
| Specific surface area: | 1615 $m^2/g$ |

On the other hand, the above-mentioned nitric acid-treated carrier has a pore distribution and a specific surface area as shown in the following table.

| | |
|---|---|
| Total pore volume: | 0.89 $cm^3/g$ |
| Pore volume with respect to pores each having a radius of less than 10 Å: | 0.45 $cm^3/g$ |
| Pore volume with respect to pores each having a radius of from 10 to 100 Å: | 0.38 $cm^3/g$ |
| Specific surface area: | 1332 $m^2/g$ |

As apparent from the above, in the case of each of the above-mentioned activated carbon "UDIAHOPE CX-2" and the above-mentioned nitric acid-treated carrier, the pore volume with respect to pores each having a radius of from 10 to 100 Å falls outside of the range required in the present invention. Specifically, in the case of each of the above-mentioned activated carbon "DIAHOPE CX-2" and the above-mentioned nitric acid-treated carrier, the pore volume with respect to the transitional pores is smaller than that of the activated carbon used in the present invention.

<Hydrogenation Reaction of a Dicarboxylic Acid Mixture>

Substantially the same procedure for hydrogenation reaction as in Example 1 was repeated except that the comparative catalyst 1 mentioned above was used as a catalyst, to thereby obtain a reaction mixture.

The obtained reaction mixture was analyzed by HPLC and GC under the conditions mentioned above to determine the conversion of the starting material and the yield of the primary alcohol. The analysis showed that the conversions of succinic acid, glutaric acid and adipic acid were 70%, 78% and 64%, respectively, and the yields of 1,4-butanediol, 1,5-pentanediol and 1,6-hexanediol were 37%, 53% and 43%, respectively.

COMPARATIVE EXAMPLE 2

<Preparation of a Catalyst>

A catalyst was prepared in accordance with the methods described in Unexamined Japanese Patent Application Laid-Open Specification Nos. 10-71332 and 10-175879.

Specifically, a catalyst was prepared in the following manner. Substantially the same procedure for carrier preparation as in Comparative Example 1 was repeated except that a 50 wt % aqueous nitric acid was used, thereby obtaining a nitric acid-treated carrier.

Substantially the same procedure for catalyst preparation as in Example 1 was repeated except that the above-obtained nitric acid-treated carrier was used as a carrier, thereby obtaining a catalyst which comprised an activated carbon having carried thereon 5.0% by weight of ruthenium and 3.5% by weight of tin. Hereinafter, this catalyst is referred to as "comparative catalyst 2".

The above-mentioned nitric acid-treated carrier has a pore distribution and a specific surface area as shown in the following table.

| | |
|---|---|
| Total pore volume: | 0.61 cm$^3$/g |
| Pore volume with respect to pores each having a radius of less than 10 Å: | 0.35 cm$^3$/g |
| Pore volume with respect to pores each having a radius of from 10 to 100 Å: | 0.23 cm$^3$/g |
| Specific surface area: | 937 m$^2$/g |

As apparent from the above, in the case of the above-mentioned nitric acid-treated carrier, the pore volume with respect to pores each having a radius of from 10 to 100 Å falls outside of the range required in the present invention. Specifically, in the case of the above-mentioned nitric acid-treated carrier, the pore volume with respect to the transitional pores is smaller than that of the activated carbon used in the present invention.

<Hydrogenation Reaction of a Dicarboxylic Acid Mixture>

Substantially the same procedure for hydrogenation reaction as in Example 1 was repeated except that the comparative catalyst 2 mentioned above was used as a catalyst, to thereby obtain a reaction mixture.

The obtained reaction mixture was analyzed by HPLC and GC under the conditions mentioned above to determine the conversion of the starting material and the yield of the primary alcohol. The analysis showed that the conversions of succinic acid, glutaric acid and adipic acid were 69%, 73% and 72%, respectively, and the yields of 1,4-butanediol, 1,5-pentanediol and 1,6-hexanediol were 21%, 40% and 36%, respectively.

COMPARATIVE EXAMPLE 3
<Preparation of a Catalyst>

A catalyst was prepared in accordance with the methods described in Unexamined Japanese Patent Application Laid-Open Specification Nos. 10-71332 and 11-60523.

Specifically, substantially the same procedure for catalyst preparation as in Example 3 was repeated except that the same nitric acid-treated carrier as obtained in Comparative Example 2 was used as a carrier, thereby obtaining a catalyst which comprised an activated carbon having carried thereon 6.1% by weight of ruthenium, 5.0% by weight of tin and 3.4% by weight of platinum. Hereinafter, this catalyst is referred to as "comparative catalyst 3".

<Hydrogenation Reaction of Succinic Acid>

5 g of ion-exchanged water, 2.10 g of succinic acid and 0.30 g of the comparative catalyst 3 mentioned above were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 15 MPa, and then hydrogenation was performed at the above-mentioned temperature under the above-mentioned hydrogen gas pressure for 5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of succinic acid was 97% and the yield of 1,4-butanediol was 47%.

EXAMPLE 8
<Hydrogenation Reaction of Succinic Acid>

5 g of ion-exchanged water, 2.10 g of succinic acid and 0.30 g of the same Ru-Sn-Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 15 MPa, and then hydrogenation was performed at the above-mentioned temperature under the above-mentioned hydrogen gas pressure for 5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of succinic acid was 98% and the yield of 1,4-butanediol was 80%.

EXAMPLE 9
<Hydrogenation Reaction of Glutaric acid>

5 g of ion-exchanged water, 2.10 g of glutaric acid and 0.30 g of the same Ru—Sn—Re catalyst as prepared in Example 2 were charged into a 30 ml autoclave. The atmosphere in the autoclave was replaced by nitrogen at room temperature, and then hydrogen gas at 2.0 MPa was introduced into the autoclave, and the internal temperature of the autoclave was elevated to 240° C. After the internal temperature of the autoclave reached 240° C., pressurized hydrogen gas was further introduced into the autoclave to increase the internal pressure thereof to 9.8 MPa, and then hydrogenation was performed at the above-mentioned temperature under the above-mentioned hydrogen gas pressure for 3.5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of glutaric acid was 100% and the yield of 1,5-pentanediol was 99%.

EXAMPLE 10
<Hydrogenation Reaction of Adipic Acid>

5 g of ion-exchanged water, 2.10 g of adipic acid and 0.30 g of the same Ru—Sn—Re catalyst as prepared in Example 2 were charged into a 30 ml autoclave. The atmosphere in the autoclave was replaced by nitrogen at room temperature, and then hydrogen gas at 2.0 MPa was introduced into the autoclave, and the internal temperature of the autoclave was elevated to 240° C. After the internal temperature of the autoclave reached 240° C., pressurized hydrogen gas was further introduced into the autoclave to increase the internal pressure thereof to 9.8 MPa, and then hydrogenation was performed at the above-mentioned temperature under the above-mentioned hydrogen gas pressure for 3.5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to deter-mine the conversion of the starting material and the yield of the primary alcohol. The analysis showed that the conversion of adipic acid was 100% and the yield of 1,6-hexanediol was 96%.

EXAMPLE 11
<Hydrogenation Reaction of Stearic Acid>

10 g of ion-exchanged water, 2.00 g of stearic acid and 0.50 g of the same Ru—Sn—Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 250° C. After the internal temperature of the autoclave reached 250° C., pressurized hydrogen gas was further introduced into the autoclave to increase the internal pressure thereof to 10 MPa, and then hydrogenation was performed at the above-mentioned temperature under the above-mentioned hydrogen gas pressure for 3.5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of stearic acid was 78% and the yield of stearyl alcohol was 74%.

EXAMPLE 12
<Hydrogenation Reaction of Maleic Acid>

7 g of ion-exchanged water, 3.00 g of maleic acid and 0.50 g of the same Ru—Sn—Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 15 MPa, and then hydrogenation was performed at the above-mentioned temperature under the above-mentioned hydrogen gas pressure for 14 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of maleic acid was 100% and the yield of 1,4-butanediol was 75%.

EXAMPLE 13
<Hydrogenation Reaction of 1,4-Cyclohexane Dicarboxylic Acid>

7 g of ion-exchanged water, 2.10 g of 1,4-cyclohexane dicarboxylic acid and 0.30 g of the same Ru—Sn—Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 230° C. After the internal temperature of the autoclave reached 230° C., pressurized hydrogen gas was further introduced into the autoclave to increase the internal pressure thereof to 9 MPa, and then hydrogenation was performed at the above-mentioned temperature under the above-mentioned hydrogen gas pressure for 3.5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of 1,4-cyclohexane dicarboxylic acid was 98% and the yield of 1,4-cyclohexane dimethanol was 75%.

EXAMPLE 14
<Hydrogenation Reaction of Terephthalic Acid>

15 g of ion-exchanged water, 2.5 g of terephthalic acid and 0.50 g of the same Ru—Sn—Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 250° C. After the internal temperature of the autoclave reached 250° C., pressurized hydrogen gas was further introduced into the autoclave to increase the internal pressure thereof to 15 MPa, and then hydrogenation was performed at the above-mentioned temperature under the above-mentioned hydrogen gas pressure for 5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of terephthalic acid was 97% and the yield of 1,4-cyclohexane dimethanol was 42%.

EXAMPLE 15
<Hydrogenation Reaction of 3-Oxobutyric Acid>

5 g of ion-exchanged water, 2.10 g of 3-oxobutyric acid and 0.30 g of the same Ru—Sn—Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 230° C. After the internal temperature of the autoclave reached 230° C., pressurized hydrogen gas was further introduced into the autoclave to increase the internal pressure thereof to 15 MPa, and then hydrogenation was performed at the above-mentioned temperature under the above-mentioned hydrogen gas pressure for 7 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of 3-oxobutyric acid was 97% and the yield of 1,3-butanediol was 78%.

EXAMPLE 16
<Hydrogenation Reaction of Maleic Anhydride>

5 g of ion-exchanged water, 2.10 g of maleic anhydride and 0.30 g of the same Ru—Sn—Re catalyst as prepared in Example 2 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 18 MPa, and then hydrogenation was performed at the above-mentioned temperature under the above-mentioned hydrogen gas pressure for 7 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of maleic anhydride was 100% and the yield of 1,4-butanediol was 87%.

EXAMPLE 17
<Hydrogenation Reaction of Succinic Acid>

5 g of ion-exchanged water, 2.10 g of succinic acid and 0.30 g of the same Ru—Sn—Pt catalyst as prepared in Example 3 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 180° C. After the internal temperature of the autoclave reached 180° C., pressurized hydrogen gas was further introduced into the autoclave to increase the internal pressure thereof to 15 MPa, and then hydrogenation was performed at the above-mentioned temperature under the above-mentioned hydrogen gas pressure for 6 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of succinic acid was 98% and the yield of 1,4-butanediol was 88%.

EXAMPLE 18
<Hydrogenation Reaction of Glutaric Acid>

5 g of ion-exchanged water, 2.10 g of glutaric acid and 0.30 g of the same Ru—Sn—Pt catalyst as prepared in Example 3 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 240° C. After the internal temperature of the autoclave reached 240° C., pressurized hydrogen gas was further introduced into the autoclave to increase the internal pressure thereof to 9.8 MPa, and then hydrogenation was performed at the above-mentioned temperature under the above-mentioned hydrogen gas pressure for 3.5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of glutaric acid was 100% and the yield of 1,5-pentanediol was 92%.

EXAMPLE 19
<Hydrogenation Reaction of Adipic Acid>

5 g of ion-exchanged water, 2.10 g of adipic acid and 0.30 g of the same Ru—Sn—Pt catalyst as prepared in Example 3 were charged into a 50 ml autoclave. The atmosphere in the autoclave was replaced by nitrogen at room temperature, and then hydrogen gas at 2.0 MPa was introduced into the autoclave, and the internal temperature of the autoclave was elevated to 240° C. After the internal temperature of the autoclave reached 240° C., pressurized hydrogen gas was further introduced into the autoclave to increase the internal pressure thereof to 9.8 MPa, and then hydrogenation was performed at the above-mentioned temperature under the above-mentioned hydrogen gas pressure for 3.5 hours.

After completion of the hydrogenation reaction, the contents of the autoclave were separated into a supernatant and the catalyst by decantation. The recovered catalyst was washed 5 times with 1 ml of ion-exchanged water, and the water used for the washing was mixed with the above-mentioned supernatant, and the resultant mixture was taken as a reaction mixture.

The obtained reaction mixture was analyzed by HPLC and GC under the conditions mentioned above to determine the conversion of the starting material and the yield of the primary alcohol. The analysis showed that the conversion of adipic acid was 100% and the yield of 1,6-hexanediol was 90%.

INDUSTRIAL APPLICABILITY

By the use of the catalyst of the present invention, a primary alcohol can be efficiently produced directly from a carboxylic acid or carboxylic anhydride by hydrogenation thereof, not through esterification thereof. Further, the catalyst of the present invention can be applied to the hydrogenation of a wide variety of carboxylic acids. Therefore, the catalyst of the present invention is extremely advantageous from the commercial viewpoint. In addition, the method of the present invention is extremely advantageous in that it is possible to use, as a starting material, waste products of various chemical processes wherein the waste products contain a large amount of a carboxylic acid or carboxylic anhydride, wherein the waste products as such may be used or, alternatively, may be subjected to appropriate treatment prior to use. For example, by using a waste product derived from an oxidation reaction mixture obtained in the production of adipic acid, various commercially useful compounds, such as 1,4-butanediol, 1,5-pentanediol and 1,6-hexanediol, can be simultaneously produced.

What is claimed is:

1. A catalyst for hydrogenating a carboxylic acid, comprising an activated carbon having carried thereon an active metal species comprising ruthenium and tin, wherein said activated carbon is produced by subjecting a carbonaceous material to activation treatment using zinc chloride, followed by calcination.

2. The catalyst according to claim 1, wherein said active metal species further comprises at least one metal selected from the group consisting of rhenium, molybdenum, platinum, palladium, silver and nickel.

3. A catalyst for hydrogenating a carboxylic acid, comprising an activated carbon having carried thereon an active metal species comprising ruthenium and tin, wherein said activated carbon, prior to having carried thereon said active metal species, exhibits the following properties (a) to (d):

(a) the total pore volume is from 1.2 to 3.0 cm$^3$/g;
(b) the pore volume with respect to pores each having a radius of less than 10 Å is from 0.03 to 0.8 cm$^3$/g;
(c) the pore volume with respect to pores each having a radius of from 10 to 100 Å is from 0.5 to 2.0 cm$^3$/g; and
(d) the specific surface area is from 800 to less than 2000 m$^2$/g.

4. The catalyst according to claim 3, wherein said active metal species further comprises at least one metal selected from the group consisting of rhenium, molybdenum, platinum, palladium, silver and nickel.

5. A method for producing a primary alcohol, which comprises reacting at least one starting material selected from the group consisting of a carboxylic acid and a carboxylic anhydride with hydrogen gas in the presence of water and a catalyst to thereby effect a catalytic hydrogenation of said starting material, said catalyst comprising an activated carbon having carried thereon an active metal species comprising ruthenium and tin, wherein said activated carbon is produced by subjecting a carbonaceous material to activation treatment using zinc chloride, followed by calcination.

6. The method according to claim 5, wherein said active metal species further comprises at least one metal selected from the group consisting of rhenium, molybdenum, platinum, palladium, silver and nickel.

7. The method according to claim 5, wherein said starting material is at least one compound selected from the group consisting of a dicarboxylic acid represented by the following formula (1):

$$\text{HOOC}-\text{R}^1-\text{COOH} \tag{1}$$

Wherein R$^1$ is a C$_2$–C$_{20}$ divalent hydrocarbon group, and a cyclic carboxylic anhydride represented by the following formula (2):

(2)

wherein R$^2$ is a C$_2$–C$_{20}$ divalent hydrocarbon group.

8. The method according to claim 5, wherein said starting material is at least one compound selected from the group consisting of succinic acid, glutaric acid, adipic acid, cyclohexane dicarboxylic acid, maleic acid, fumaric acid, terephthalic acid, succinic anhydride and maleic anhydride.

9. The method according to claim 5, wherein said starting material is a dicarboxylic acid mixture comprising succinic acid, glutaric acid and adipic acid.

10. The method according to claim 9, wherein said dicarboxylic acid mixture is derived from a reaction mixture obtained by subjecting at least one compound selected from the group consisting of cyclohexanone and cyclohexanol to oxidation reaction.

11. The method according to claim 5, wherein said catalytic hydrogenation is conducted under conditions wherein the temperature is from 100 to 300° C. and the hydrogen pressure is from 1 to 25 MPa.

12. A method for producing a primary alcohol, which comprises reacting at least one starting material selected from the group consisting of a carboxylic acid and a carboxylic anhydride with hydrogen gas in the presence of water and a catalyst to thereby effect a catalytic hydrogenation of said starting material, said catalyst comprising an activated carbon having carried thereon an active metal species comprising ruthenium and tin, wherein said activated carbon, prior to having carried thereon said active metal species, exhibits the following properties (a) to (d):

(a) the total pore volume is from 1.2 to 3.0 cm$^3$/g;
(b) the pore volume with respect to pores each having a radius of less than 10 Å is from 0.03 to 0.8 cm$^3$/g;

(c) the pore volume with respect to pores each having a radius of from 10 to 100 Å is from 0.5 to 2.0 cm$^3$/g; and (d) the specific surface area is from 800 to less than 2000 m$^2$/g.

13. The method according to claim 12, wherein said active metal species further comprises at least one metal selected from the group consisting of rhenium, molybdenum, platinum, palladium, silver and nickel.

14. The method according to claim 12, wherein said starting material is at least one compound selected from the group consisting of a dicarboxylic acid represented by the following formula (1):

wherein R$^1$ is a C$_2$–C$_{20}$ divalent hydrocarbon group, and a cyclic carboxylic anhydride represented by the following formula (2):

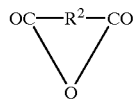

wherein R$^2$ is a C$_2$–C$_{20}$ divalent hydrocarbon group.

15. The method according to claim 12, wherein said starting material is at least one compound selected from the group consisting of succinic acid, glutaric acid, adipic acid, cyclohexane dicarboxylic acid, maleic acid, fumaric acid, terephthalic acid, succinic anhydride and maleic anhydride.

16. The method according to claim 12, wherein said starting material is a dicarboxylic acid mixture comprising succinic acid, glutaric acid and adipic acid.

17. The method according to claim 16, wherein said dicarboxylic acid mixture is derived from a reaction mixture obtained by subjecting at least one compound selected from the group consisting of cyclohexanone and cyclohexanol to oxidation reaction.

18. The method according to claim 12, wherein said catalytic hydrogenation is conducted under conditions wherein the temperature is from 100 to 300° C. and the hydrogen pressure is from 1 to 25 MPa.

* * * * *